United States Patent [19]

Coates et al.

[11] Patent Number: 4,528,371

[45] Date of Patent: Jul. 9, 1985

[54] PROCESS FOR PREPARING 6-(2-HYDROXYPHENYL)-3-PYRIDAZINONE

[75] Inventors: William J. Coates; Brian H. Warrington, both of Welwyn Garden City, England

[73] Assignee: Smith Kline & French Laboratories Limited, Welwyn Garden City, England

[21] Appl. No.: 504,204

[22] Filed: Jun. 14, 1983

[30] Foreign Application Priority Data

Jun. 24, 1982 [GB] United Kingdom ............ 8218373

[51] Int. Cl.$^3$ ................... C07D 237/08; C07C 59/48
[52] U.S. Cl. ................................. 544/239; 562/463
[58] Field of Search .......................... 544/239

[56] References Cited

U.S. PATENT DOCUMENTS

| | | | |
|---|---|---|---|
| 4,053,601 | 10/1977 | Coates et al. | 424/250 |
| 4,111,936 | 9/1978 | Coates et al. | 544/239 |
| 4,152,517 | 5/1979 | Levinson et al. | 544/239 |

FOREIGN PATENT DOCUMENTS

| | | | |
|---|---|---|---|
| 2207517 | 12/1972 | Fed. Rep. of Germany | 544/239 |
| 2435244 | 2/1976 | Fed. Rep. of Germany | 544/239 |
| 2614827 | 10/1977 | Fed. Rep. of Germany | |
| 2819798 | 11/1979 | Fed. Rep. of Germany | |

OTHER PUBLICATIONS

Wermuth et al, Chim. Ther., vol. 5(2), (1970), pp. 141-145.
Pettit et al, J. Org. Chem., vol. 35(5), (1970), pp. 1367-1376.
Derwent Abstract 80380Y, (Abstract of Japanese Patent J5 2116-485).
Hasegawa et al, Chem. Pharm. Bulletin, 25:192-195, (1977).
Fieser et al, "Reagents for Organic Synthesis", vol. 1, p. 441, (John Wiley & Sons, New York).

Primary Examiner—Donald G. Daus
Assistant Examiner—William A. Teoli, Jr.
Attorney, Agent, or Firm—Joan S. Keps; Richard D. Foggio; Alan D. Lourie

[57] ABSTRACT

A process for preparing 6-(2-hydroxyphenyl)-3-pyridazinone which comprises reacting 2-hydroxyacetophenone with glyoxylic acid under alkaline conditions, adjusting the pH of the reaction mixture to give a mixture within a pH range of about pH 4.0-9.5 and which contains a weak base, and subsequently reacting with hydrazine.

6-(2-Hydroxyphenyl)-3-pyridazinone is a useful intermediate in the preparation of anti-hypertensive agents.

8 Claims, No Drawings

PROCESS FOR PREPARING 6-(2-HYDROXYPHENYL)-3-PYRIDAZINONE

The present invention relates to a process for the preparation of pyridazinone derivatives, in particular 6-(2-hydroxyphenyl)-3-pyridazinone (formula I). This compound is a useful intermediate in the preparation of anti-hypertensive agents, for example see the disclosures of U.S. Pat. No. 4,053,601.

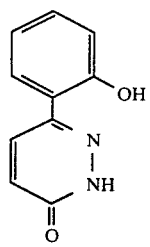

(I)

In general the processes disclosed in the aforementioned U.S. patent comprises a Friedel-Crafts acylation reaction. It is well known that such reactions often result in the production of isomeric mixtures of products with attendant difficulties of isolation and purification resulting in reduced efficiency and decreased economic attractiveness of the process.

Hasegawa et al. Chem. Pharm. Bulletin 25 192 (1977) outline a process for preparing the compound of the formula (I) but this comprises a lengthy preparation of 3-hydroxypyridazine 1-oxide and subsequently reacting with benzyne and rearranging.

West German Offenlegungsschrift No. 2,614,827 (Lentia) claims a process for the preparation of 3-phenylpyridazin-6-one (formula (II)) which comprises the reaction with hydrazine hydrate in aqueous solution of the ammonium salt of 2-hydroxy-4-oxo-4-phenyl-butyric acid of the formula (III).

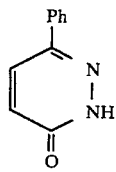

(II)

Ph—CO—CH$_2$—CH(OH)—CO$_2$$^\ominus$NH$_4$$^\oplus$ (III)

The compound of the formula (III) is stated to be prepared via the reaction of 3 equivalents of acetophenone with solid glyoxylic acid hydrate, followed by neutralisation of the reaction mixture with NH$_3$ and removal of the unreacted acetophenone. West German Offenlegungsschrift No. 2,819,798 from the same company states that undesirable side-reactions occur in the first mentioned aspect of the process as 2-hydroxy-4-oxo-4-phenylbutyric acid is unstable in alkali and breakdown products such as acetophenone and glyoxylic acid are formed which react with hydrazine reducing the yield.

Adaptation of the conditions described in West German Offenlegungsschrift No. 2,614,827 to the preparation of 6-(2-hydroxyphenyl)-3-pyridazinone from 2-hydroxy acetophenone afforded an unsatisfactory yield of about 33% which was not significantly improved with longer reaction time or increased glyoxylic acid. On the other hand however, application of the conditions of OLS No. 2,614,827 to the corresponding 3-hydroxyphenyl and 4-hydroxyphenyl compounds afforded good yields of the pyridazinone products.

The object of the present invention is to provide a process that affords 6-(2-hydroxyphenyl)-3-pyradazinone in relatively high yield with greater ease then existing processes, where about one equivalent of 2-hydroxyacetophenone is required, and without the need for the isolation and/or purification of intermediates. Surprisingly we have found that these requirements may be met by the reaction of glyoxylic acid and 2-hydroxyacetophenone under basic conditions, with subsequent reaction with hydrazine.

Accordingly, the present invention provides a process for the preparation of 6-(2-hydroxyphenyl)-3-pyridazinone which comprises reacting 2-hydroxyacetophenone with glyoxylic acid under alkaline conditions, adjusting the pH of the reaction mixture to give a mixture within a pH range of about pH 4.0–9.5 and which contains a weak base, and subsequently reacting with hydrazine.

It is believed that the reaction proceeds via the intermediacy of 2-hydroxy-4-oxo-4-(2-hydroxyphenyl)-butyric acid of the formula (IV) and/or a salt thereof:

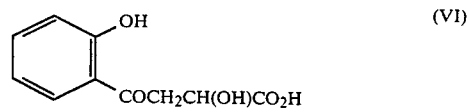

(VI)

The 2-hydroxyacetophenone and glyoxylic acid are suitably reacted in strongly alkaline conditions, for example between pH 10 and 13. This is conveniently achieved by the use of a hydroxide, for example sodium hydroxide or potassium hydroxide, in excess of the amount required to neutralise the reactants.

The glyoxylic acid is conveniently used in the form of a 50% aqueous solution as this is commercially available, although of course it may be generated in situ.

This stage of the reaction is suitably performed at a temperature between 0° C. and 35° C., for example between 15° C. and 25° C.

As previously mentioned a particularly favoured aspect of this invention is that approximately one equivalent of 2-hydroxyacetophenone is used; thus suitably the molar ratio of 2-hydroxyacetophenone to glyoxylic acid is about 0.7:1.0 to 1.5:1.0, more suitably 0.9:1.0 to 1.2:1.0 and preferably 1.0:1.0.

After the reaction of 2-hydroxyacetophenone and glyoxylic acid is substantially complete, for example this may be shown by standard assay procedures (for example high pressure liquid chromatography), the reaction mixture is taken to about pH 4.0 to 9.5, preferably between pH 6.5 and 8.5. Any unreacted 2-hydroxyacetophenone may be removed at this stage by separation into an organic solvent such as a chlorinated hydrocarbon for example dichloromethane. Alternatively, or additionally, steam distillation may be utilised to remove unwanted 2-hydroxyacetophenone.

Before the reaction mixture is reacted with hydrazine, a salt of a weak base, for example an ammonium or substituted ammonium salt, is introduced into the reaction mixture in order to achieve a "buffered effect", so that the reaction with hydrazine is performed in the presence of a weak base. By a weak base we mean a base that allows a significant amount of the free acid of the formula (IV) to exist in equilibrium with a salt of the compound of the formula (IV). Preferably at least one mole equivalent of the weak base is present.

One way of achieving this is to use an ammonium salt, for example ammonium acetate, ammonium chloride, or ammonium sulphate; or a substituted ammonium salt for example a mono-, di- or tri-($C_{1-10}$)alkyl-ammonium salt for example methylammonium hydrochloride, dimethylammoniumhydrochloride or tri-ethylammonium hydrochloride. In addition hydrazine salts for example hydrazine hydrochloride and hydrazine sulphate may be used in achieving the desired "buffered effect".

Another way of achieving the "buffered effect" is to lower the pH of the reaction mixture to below 6.0, and more suitably to below 4.5. This may be performed by the use of an acid, for example hydrochloric acid, sulphuric acid or acetic acid. The reaction mixture is then taken back to the desired pH, for example to pH 7.0–8.5, whereupon hydrazine is added. In one embodiment this increase in pH is conveniently carried out using ammonia, either in gaseous form or in aqueous form, so that the ammonium salt of 2-hydroxy-4-oxo-4-(2-hydroxyphenyl)butyric acid is thought to be formed in equilibrium with the free acid.

The next stage of the overall reaction involves treatment with hydrazine or its chemical equivalent. Suitably hydrazine is introduced to the reaction mixture in the form of an aqueous solution. In an alternative hydrazine hydrate may be used. This cyclisation stage of the overall reaction to form the desired 6-(2-hydroxyphenyl)-3-pyridazinone is believed to proceed via the compound of the formula (V) which dehydrates under the reaction conditions.

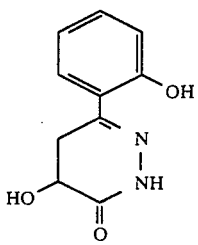

(V)

The cyclisation and subsequent dehydration reaction take place at about pH 4.0–9.5, preferably between pH 6.5 and 8.5, at an elevated temperature, most conveniently at reflux temperature which is is about 100° C. The progress of this stage of the reaction may be monitored in conventional manner, for example by high pressure liquid chromatography.

We have found, in yet another favourable aspect of this invention, that when the reaction is performed at an alkaline pH the desired product tends to separate out of the hot reaction mixture, whereas the majority of any impurities tend to be acidic and stay in solution. Thus isolation and purification of the product is greatly facilitated.

In another aspect of this invention we provide a process for the preparation of 6-(2-hydroxyphenyl)-3-(2H)-pyridazinone which comprises the reaction of a compound of the formula (IV) with hydrazine at a pH of 4.0 to 9.5. Preferably such a reaction is performed at a pH of between 6.5 and 8.5. Preferably the compound of the formula (IV) is in equilibrium with an ammonium salt thereof.

The compound of the formula (IV) and salts thereof are novel and as such form part of the invention.

The following Examples serve to illustrate the invention. Temperatures are recorded in degrees Celsius.

EXAMPLE 1

(i) An aqueous solution of potassium hydroxide (20% w/v) was added dropwise to a stirred mixture, of glyoxylic acid hydrate (9.2 g, 0.1 mol) and water (2.2 ml) cooled in an ice-bath, until the pH of the mixture was 9. To this stirred solution was added a partial solution of 2-hydroxyacetophenone (13.6 g, 0.1 mol) in aqueous potassium hydroxide (10 g, 0.18 mol, in 40 ml water) and the mixture was stirred at room temperature for 2.5 hours. The mixture was acidified to pH 8 (with cooling) by the addition of acetic acid (approximately 7 ml) and extracted with dichloromethane (4×30 ml). The organic extracts were evaporated to give unreacted 2-hydroxyacetophenone (1.55 g, 11%).

(ii) The aqueous solution was adjusted to pH 4.5 by the addition of acetic acid (approximately 15 ml) and then adjusted to pH 8 by the addition of aqueous ammonia (28% w/w, approximately 25 ml); hydrazine hydrate (5 ml 0.1 mol) was added, and the mixture was stirred and heated under reflux for 2 hours. The solid which crystallised on cooling was filtered off to give 6-(2-hydroxyphenyl)-3(2H)-pyridazinone (12.13 g, 64.5%) m.p. 289°–302°. This product tended to sublime and the sublimate had m.p. 303°–306°.

EXAMPLE 2

A 20% w/v solution of potassium hydroxide cooled to 5° was added slowly to a cooled (5°) 50% aqueous solution of glyoxylic acid (1184 g, 8 mol) until the mixture had pH 9, with external cooling to maintain the temperature below 25°. 2-Hydroxyacetophenone (1089 g, 8 mol) was poured into a solution of potassium hydroxide (783 g) in water (2580 ml), this mixture was added to the glyoxylic acid-potassium hydroxide solution and the resultant mixture was stirred at room temperature for 4 hours. The pH was adjusted to pH 8, with external cooling, by the addition of concentrated sulphuric acid (330 ml). An inorganic sediment was removed by filtration, the filtrate was extracted with dichloromethane (3000 ml) and concentrated sulphuric acid (100 ml) was added with external cooling to the aqueous phase to give a mixture with pH 4.5. A solid precipitated out during this process. Concentrated aqueous ammonia (28% w/w) was added with external cooling until the mixture had pH 8. The precipitate dissolved during this addition. Aqueous hydrazine hydrate (64% w/w, 402.4 g, 8 mol) was added, the mixture was heated under reflux for 3 hours and allowed to cool to room temperature. The solid was filtered off, washed with water and 2-propanol and dried to give 6-(2-hydroxyphenyl)-3(2H)-pyridazinone (811 g, 54%) m.p. 294°.

EXAMPLE 3

One half of an aqueous solution prepared in an identical manner to that described in Example 1 was adjusted to pH 4.5 with acetic acid and the solid which separated out was filtered off. The filtrate was extracted repeatedly with ethyl acetate, adjusted to pH 1 with hydrochloric acid and further extracted with ethyl acetate. The combined organic extracts were washed twice with brine and then extracted with aqueous ammonia. The aqueous ammonia extract was extracted with dichloromethane and the solid isolated above was added to the aqueous phase to give a solution of the ammonium salt of 2-hydroxy-4-oxo-4-(2-hydroxyphenyl)butyric acid at pH 8. Hydrazine hydrate (2.5 ml, 0.05 mole) was added and the mixture was heated under reflux for 2 hours. The solid which separated out was filtered off to give 6-(2-hydroxyphenyl)-3(2H)-pyridazinone (5.79 g, 62%) m.p. 296°-302°.

EXAMPLE 4

Glyoxylic acid hydrate (18.4 g) was added to a cooled (10° C.), stirred solution of potassium hydroxide (31.36 g) in water (150 ml). To this solution was added 2-hydroxyacetophenone (24 ml) and the resultant solution was stirred at room temperature for 2½ hours. The reaction mixture was divided into two equal aliquots, to one of which was added concentrated hydrochloric acid (approximately 16 ml) until pH 8 was attained. This solution was then washed with dichloromethane (4×25 ml) and the aqueous layer divided into two equal aliquots. One of these aliquots was stirred in the cold with ethyl acetate (60 ml), and concentrated hydrochloric acid (5 ml) added in two batches to firstly take the pH to 2–3 and secondly to take the pH to 1–2. The ethyl acetate layer was separated and the aqueous layer further extracted with ethyl acetate (2×30 ml). The combined ethyl acetate extracts were washed with water, brine, dried (MgSO$_4$) and evaporated under reduced pressure to afford a viscous oil which solidified on seeding to yield a solid (6.2 g, 66%). Trituration with ether gave a white solid which was collected by filtration and washed with ether. This solid was 2-hydroxy-4-oxo-4-(2-hydroxyphenyl)butyric acid, m.p. 90°–92° C.

EXAMPLE 5

To a stirred suspension of 2-hydroxy-4-oxo-4-(2-hydroxyphenyl)butyric acid in water was added ammonia until pH 7.0 was attained. Hydrazine was added slowly with the concurrent addition of sufficient glacial acetic acid to maintain a pH of 7.0. Steam heating was applied for 2 hours and during this time the pH of 7.0 was maintained by the addition of ammonia as necessary. The reaction mixture was allowed to cool to room temperature. The solid was filtered off, washed with water, 2-propanol and dried (MgSO$_4$) to afford 6-(2-hydroxyphenyl)-3(2H)-pyridazinone (85%).

EXAMPLE 6

To a stirred suspension of 2-hydroxy-4-oxo-4-(2-hydroxyphenyl)butyric acid (0.025M) in water (20 ml) was added triethylamine (3.3 ml), taking the pH to 9.5, followed by concentrated hydrochloric acid (2.5 ml) to take the pH to 4. Hydrazine (0.05M) was added slowly with the concurrent addition of sufficient glacial acetic acid to maintain a pH of 7.0. Steam heating was applied for 2 hours and during this time the pH of 7.0 was maintained by the addition of ammonia as necessary. The reaction mixture was allowed to cool to room temperature. The solid was filtered off, washed with water, 2-propanol and dried to afford 6-(2-hydroxyphenyl)-3(2H)-pyridazinone (78.3%).

EXAMPLE 7

(i) To a cooled (10° C.), stirred solution of potassium hydroxide (47.2 g) in water (400 ml) was added 50% aqueous solution of glyoxylic acid (43.2 g) and 2-hydroxyacetophenone (40.8 g). The reaction mixture was stirred at room temperature for 4 hours, taken to pH 7 and washed with dichloromethane (2×100 ml). The aqueous layer was divided into two equal aliquots.

(ii) One of these aliquots was treated with 35% aqueous solution of hydrazine (13.8 ml), 25% aqueous solution of dimethylamine (54 ml) and concentrated hydrochloric acid (30 ml). The mixture was heated under reflux for 2½ hours, and allowed to cool to room temperature. The solid was filtered off, washed with water, 2-propanol and dried to afford 6-(2-hydroxyphenyl)-3(2H)-pyridazinone (58.3%).

EXAMPLE 8

To an aliquot obtained in the same manner as that of Example 7(i) was added ammonium acetate (1 mole equivalent) and hydrazine as a 35% aqueous solution (1 mole equivalent). Steam heating was applied for 2 hours with maintenance of the pH at 7.0. The reaction mixture was allowed to cool to room temperature. The solid was filtered off, washed with water, 2-propanol and dried to afford 6-(2-hydroxy-phenyl)-3(2H)-pyridazinone (63.8%).

What we claim is:

1. A process for preparing 6-(2-hydroxyphenyl)-3-pyridazinone which comprises reacting 2-hydroxyacetophenone with glyoxylic acid under alkaline conditions, adjusting the pH of the reaction mixture to give a mixture within a pH range of about pH 4.0–9.5 and which contains a weak base, and subsequently reacting with hydrazine.

2. A process according to claim 1 wherein 2-hydroxyacetophenone and glyoxylic acid are reacted in strongly alkaline conditions.

3. A process according to claim 1 wherein the glyoxylic acid is introduced into the reaction mixture as a 50% aqueous solution.

4. A process according to claim 1 wherein the molar ratio of 2-hydroxyacetophenone to glyoxylic acid is about 0.7:1.0 to 1.5:1.0.

5. A process according to claim 4 wherein the molar ratio is about 1.0:1.0.

6. A process according to claim 1 wherein the weak base is an ammonium or substituted ammonium salt.

7. A process according to claim 1 wherein the pH of the reaction mixture is taken to a range within 6.5–8.5.

8. A process according to claim 1 wherein the desired pH is achieved by lowering the pH below 4.5 and treating with ammonia.

* * * * *